US011166637B2

(12) United States Patent
Siedenburg

(10) Patent No.: US 11,166,637 B2
(45) Date of Patent: Nov. 9, 2021

(54) NON-INVASIVE BLOOD PRESSURE MEASUREMENT USING PULSE WAVE VELOCITY

(71) Applicant: Stryker Corporation, Kalamazoo, MI (US)

(72) Inventor: Clinton T. Siedenburg, Everett, WA (US)

(73) Assignee: Stryker Corporation, Kalamazoo, MI (US)

( * ) Notice: Subject to any disclaimer, the term of this patent is extended or adjusted under 35 U.S.C. 154(b) by 512 days.

(21) Appl. No.: 15/874,796

(22) Filed: Jan. 18, 2018

(65) Prior Publication Data

US 2018/0199834 A1  Jul. 19, 2018
US 2019/0014997 A9  Jan. 17, 2019

Related U.S. Application Data

(60) Provisional application No. 62/447,780, filed on Jan. 18, 2017.

(51) Int. Cl.
*A61B 5/021* (2006.01)
*A61B 8/06* (2006.01)
(Continued)

(52) U.S. Cl.
CPC ........ *A61B 5/02125* (2013.01); *A61B 5/0261* (2013.01); *A61B 5/0285* (2013.01);
(Continued)

(58) Field of Classification Search
None
See application file for complete search history.

(56) References Cited

U.S. PATENT DOCUMENTS 4,336,808 A * 6/1982 Ohno ................ A61B 8/06
600/459
5,249,577 A * 10/1993 Shinomura ........ A61B 8/06
600/441
(Continued)

FOREIGN PATENT DOCUMENTS

EP         898938 A2    3/1999
WO   WO2008050334 A2   5/2008
(Continued)

OTHER PUBLICATIONS

Tijsseling et al., "Johannes von Kries and the History of Water Hammer" Journal of Hydraulic Engineering-ASCE, vol. 133, Jan. 2007. (Year: 2007).*
(Continued)

*Primary Examiner* — Yi-Shan Yang
(74) *Attorney, Agent, or Firm* — Lee & Hayes, P.C.

(57) ABSTRACT

A method and apparatus to non-invasively measure instantaneous blood pressure using pulse wave velocity are disclosed. A measurement component is affixed to a patient proximate to a blood vessel. One or more sensors, such as an ultrasound sensor, is included in the measurement component. The measurement component substantially simultaneously measures the pulse wave velocity of the vessel and the instantaneous blood velocity within the vessel. The measurement component computes the instantaneous blood pressure of the vessel using, for example, the water hammer equation. The one or more sensors may be contained in a disposable patch or collocated with another sensor, such as a patient-monitor sensor, or the like.

37 Claims, 8 Drawing Sheets

(51) Int. Cl.

| | |
|---|---|
| *A61B 5/00* | (2006.01) |
| *A61B 8/04* | (2006.01) |
| *A61B 8/08* | (2006.01) |
| *A61N 1/39* | (2006.01) |
| *A61B 8/00* | (2006.01) |
| *A61B 50/30* | (2016.01) |
| *A61B 5/026* | (2006.01) |
| *A61B 5/0295* | (2006.01) |
| *A61B 5/1455* | (2006.01) |
| *A61B 8/02* | (2006.01) |
| *A61B 5/0285* | (2006.01) |
| *A61B 6/00* | (2006.01) |

(52) U.S. Cl.
CPC ........ *A61B 5/0295* (2013.01); *A61B 5/14551* (2013.01); *A61B 5/486* (2013.01); *A61B 5/7225* (2013.01); *A61B 5/7278* (2013.01); *A61B 6/4405* (2013.01); *A61B 8/02* (2013.01); *A61B 8/04* (2013.01); *A61B 8/06* (2013.01); *A61B 8/4227* (2013.01); *A61B 8/4281* (2013.01); *A61B 8/4416* (2013.01); *A61B 8/4427* (2013.01); *A61B 8/4483* (2013.01); *A61B 8/5223* (2013.01); *A61B 8/56* (2013.01); *A61B 50/30* (2016.02); *A61N 1/3925* (2013.01); *A61N 1/39044* (2017.08); *A61B 8/0891* (2013.01)

(56) References Cited

U.S. PATENT DOCUMENTS

| | | | |
|---|---|---|---|
| 5,309,916 A | 5/1994 | Hatschek | |
| 5,535,747 A | 7/1996 | Katakura | |
| 6,176,832 B1* | 1/2001 | Habu | A61B 5/0285 600/485 |
| 6,261,233 B1* | 7/2001 | Kantorovich | A61B 8/06 600/454 |
| 6,419,632 B1* | 7/2002 | Shiki | A61B 8/06 600/443 |
| 6,676,600 B1* | 1/2004 | Conero | A61B 5/00 600/438 |
| 7,125,383 B2 | 10/2006 | Hoctor et al. | |
| 7,306,563 B2* | 12/2007 | Huang | A61B 5/021 600/485 |
| 7,621,876 B2 | 11/2009 | Hoctor et al. | |
| 7,815,574 B2 | 10/2010 | Mourad et al. | |
| 8,738,128 B2 | 5/2014 | Pearce et al. | |
| 9,161,701 B2 | 10/2015 | Lading | |
| 10,722,209 B2 | 7/2020 | Chen et al. | |
| 2002/0177781 A1 | 11/2002 | Amano | |
| 2005/0131282 A1 | 6/2005 | Brodnick et al. | |
| 2005/0143640 A1 | 6/2005 | Hoctor et al. | |
| 2006/0211942 A1 | 9/2006 | Hoctor et al. | |
| 2007/0093702 A1 | 4/2007 | Yu et al. | |
| 2007/0167844 A1 | 7/2007 | Asada et al. | |
| 2011/0040197 A1 | 2/2011 | Welch et al. | |
| 2012/0123246 A1 | 5/2012 | King et al. | |
| 2014/0200423 A1 | 7/2014 | Eisen et al. | |
| 2015/0073230 A1 | 3/2015 | Stergiou | |
| 2015/0327785 A1 | 11/2015 | Lading et al. | |
| 2015/0327786 A1 | 11/2015 | Lading et al. | |
| 2016/0030758 A1 | 2/2016 | Guiney et al. | |
| 2016/0038117 A1 | 2/2016 | Tamada | |
| 2016/0262639 A1 | 9/2016 | Ukawa | |
| 2016/0287095 A1 | 10/2016 | Gu | |
| 2016/0345930 A1 | 12/2016 | Mizukami et al. | |
| 2017/0000688 A1 | 1/2017 | Kaufman et al. | |
| 2017/0042504 A1* | 2/2017 | Rich | A61B 8/04 |
| 2017/0172429 A1 | 6/2017 | Takoh et al. | |
| 2017/0273664 A1* | 9/2017 | Baym | A61B 8/429 |
| 2017/0360313 A1 | 12/2017 | Baek et al. | |
| 2018/0078155 A1 | 3/2018 | Baek et al. | |
| 2018/0110667 A1* | 4/2018 | Freeman | A61G 7/05 |
| 2018/0199834 A1 | 7/2018 | Siedenburg | |
| 2018/0224534 A1* | 8/2018 | Schulte | G01S 7/521 |
| 2018/0235567 A1 | 8/2018 | Bezemer et al. | |
| 2018/0369065 A1 | 12/2018 | Siedenburg et al. | |
| 2019/0053779 A1 | 2/2019 | Siedenburg | |
| 2019/0125191 A1 | 5/2019 | Siedenburg | |

FOREIGN PATENT DOCUMENTS

| | | |
|---|---|---|
| WO | WO2016081517 A2 | 5/2016 |
| WO | WO2017032648 A1 | 3/2017 |

OTHER PUBLICATIONS

International Search Report & Written Opinion, dated Jan. 25, 2018; International Application No. PCT/US2017/60708, filed Nov. 8, 2017; 9 pages.

International Search Report & Written Opinion, dated Apr. 17, 2018; International Application No. PCT/US2018/014273, filed Jan. 18, 2018; pp. 1-14.

Beulen et al. "Toward Noninvasive Blood Pressure Assessment in Arteries by Using Ultrasound", Ultrasound in Med. & Biol., vol. 37, No. 5, pp. 788-797, 2011.

Murgo et al. "Aortic Input Impedance in Normal Man: Relationship to Pressure Wave Forms", American Heart Association, 1980, pp. 105-116.

Pereira et al., "Novel Methods for Pulse Wave Velocity Measurement", Physics Dept. Instrumentation Center, Univ. of Coimbra, Rua Larga, Coimbgra, PT. J. Med Biol. Eng. (2015) 555-565.

Soleimani et al. "Assessing the Blood Pressure Waveform of the Carotid Artery Using an Ultrasound Image Processing Method" Univ. of Tehran, IR, Ultrasonography 2017, pp. 144-152.

Struijk et al. "Blood Pressure Estimation in the Human Fetal Descending Aorta", Wiley InterScience, Ultrasound Obstet Gynecol 2008, pp. 673-681.

Vennin et al., "Noninvasive calculation fo the aortic blood pressure waveform from the flow velocity waveform: a proof of concept", Am J Physiol Heart Circ Physiol 309: H969-H976, 2015. First published Jul. 10, 2015.

O'Rourke, "Vascular Impedance in Studies of Arterial and Cardiac Function", School of Medicine, University of New South Wales, St. Vincent's Hospital, Sydney, Australia, Physiological Reviews, vol. 62, No. 2, Apr. 1982, pp. 571-623.

Office Action for U.S. Appl. No. 16/167,195, dated Jun. 4, 2021, Siedenburg, "Light-Based Non-Invasive Blood Pressure Systems and Method", 12 pages.

Office Action for U.S. Appl. No. 16/103,797, dated Apr. 28, 2021, Siedenburg, "Constitutive Equation for Non-Invasive Blood Pressure Measurement Systems and Methods", 16 pages.

U.S. Appl. No. 15/999,038, filed Aug. 16, 2018, titled "Non-invasive blood pressure measurement devices, systems and methods".

U.S. Appl. No. 16/103,797, filed Aug. 14, 2018, titled "Constitutive equation for non-invasive blood pressure measurement systems and methods".

Bercoff, et al., "Supersonic Shear Imaging: A New Technique for Soft Tissue Elasticity Mapping," IEEE Transactions on Ultrasonics, Ferroelectrics, and Frequency Control, vol. 51, No. 4, Apr. 2004, pp. 396-409.

Bernal, et al., "Material Property Estimation for Tubes and Arteries Using Ultrasound Radiation Force and Analysis of Propagating Modes," Journal of the Acoustical Society of America, vol. 129(3), Mar. 2011, pp. 1344-1354.

The European Office Action dated Jan. 12, 2021 for European Patent Application No. 18703419.4, a counterpart foreign application of U.S. Appl. No. 15/874,796, 5 pages.

Hoeks, et al., "Non-Invasive Measurement of Mechanical Properties of Arteries in Health and Disease", Proceedings of the Institution of Mechanical Engineers, Part H: Journal of Engineering in Medicine, Mar. 1999, vol. 213 Part H, pp. 195-202.

(56) References Cited

OTHER PUBLICATIONS

Jensen, J., "Comparison of Vector Velocity Imaging Using Directional Beamforming and Transverse Oscillation for a Convex Array Transducer," SPIE Medical Imaging, San Diego, CA, Feb. 2014, p. 904012-1 to 904012-8.
Meinders, et al., "Simultaneous Assessment of Diameter and Pressure Waveforms in the Carotid Artery," Ultrasound in Medicine and Biology, vol. 30, No. 2, Feb. 2004, pp. 147-154.
Messas, et al., "Arterial Wall Elasticity: State of the Art and Future Prospects," Diagnostic and Interventional Imaging, Apr. 2013, pp. 561-569.
Montaldo, et al., "Ultrafast Compound Doppler Imaging: A New Approach of Doppler Flow Analysis," 2010 IEEE International Symposium on Biomedical Imaging: From Nano to Macro, Apr. 2010, pp. 324-327.
Office Action for U.S. Appl. No. 16/103,797, dated Dec. 16, 2020, Siedenburg, "Constitutive Equation for Non-Invasive Blood Pressure Measurement Systems and Methods", 16 pages.
Office Action for U.S. Appl. No. 16/167,195, dated Feb. 1, 2021, Siedenburg, "Light-Based Non-Invasive Blood Pressure Systems and Method", 10 pages.
Office Action for U.S. Appl. No. 15/999,038, dated Mar. 25, 2021, Siedenburg, "Non-invasive blood pressure measurement devices, systems and methods", 27 pages.
Qi, et al., "Phase-Resolved Acoustic Radiation Force Optical Coherence Elastography," Journal of Biomedical Optics, vol. 17( 11), Nov. 2012, p. 110505-1 to 110505-3.
Rabben, et al., "An Ultrasound-Based Method for Determining Pulse Wave Velocity in Superficial Arteries," Journal of Biomechanics, vol. 37, Oct. 2004, pp. 1615-1622.
Rajan, et al., "Review of methodological developments in laser Doppler flowmetry," Lasers Med Sci, 24:269-283, Mar. 2009.

\* cited by examiner

TREATMENT SCENE

Handheld NIBP Monitor

Wearable NIBP Monitor

Monitor/Defibrillator

Ultrasound Machine

COMPONENTS OF VITAL SIGNS MONITOR

NON-INVASIVE BLOOD PRESSURE MEASUREMENT USING PULSE WAVE VELOCITY

CROSS-REFERENCE TO RELATED APPLICATIONS

This patent application claims the benefit of and priority to U.S. Provisional Patent Application Ser. No. 61/447,780 filed on Jan. 18, 2017, entitled "Non-Invasive Blood Pressure (NIPB) Using Pulse Wave Velocity (PWV)," the disclosure of which are hereby incorporated by reference for all purposes.

BACKGROUND

Knowing a patient's blood pressure is a critical component of medical care. Blood pressure is such an important vital sign that the occasions where it is urgently needed to determine therapy broadly range from chaotic emergency situations in the field to anesthesiology in the carefully controlled operating room to home monitoring and research. In some applications, it is desirable to measure the blood pressure at the resolution of each heartbeat.

This disclosure distinguishes between two general types of blood pressure measurements: Invasive blood pressure measurement and non-invasive blood pressure measurement. Invasive blood pressure measurement requires catheterization of a vessel. Such invasive procedures almost always come with the attendant risk of complications as well as the increased expense of materials and labor. While it may sometimes be necessary, invasive blood pressure measurement should be avoided if sufficient non-invasive means are available.

Non-invasive methods of determining blood pressure typically require the use of a cuff that restricts blood flow in the patient's appendage in which the blood pressure is being measured. There are several limitations with traditional non-invasive blood pressure measurement methods. One limitation is that non-invasive blood pressure measurement requires minimum rest periods between recurring measurements to obtain acceptable levels of clinical accuracy. Another limitation is that a typical non-invasive blood pressure devices is cumbersome to deploy and manage. Still another limitation is that conventional NIBP devices that use automated means are prone to error in either failing to obtain a measurement altogether or obtaining an inaccurate measurement due to motion and bumping of a sensitive component, such as a hose, of the NIBP device, during use. Often, the devices are subject to movement and bumping during transport and treatment of the patient, such as when a patient is being transported in an emergency vehicle, for example.

DETAILED DESCRIPTION

Figure 1:
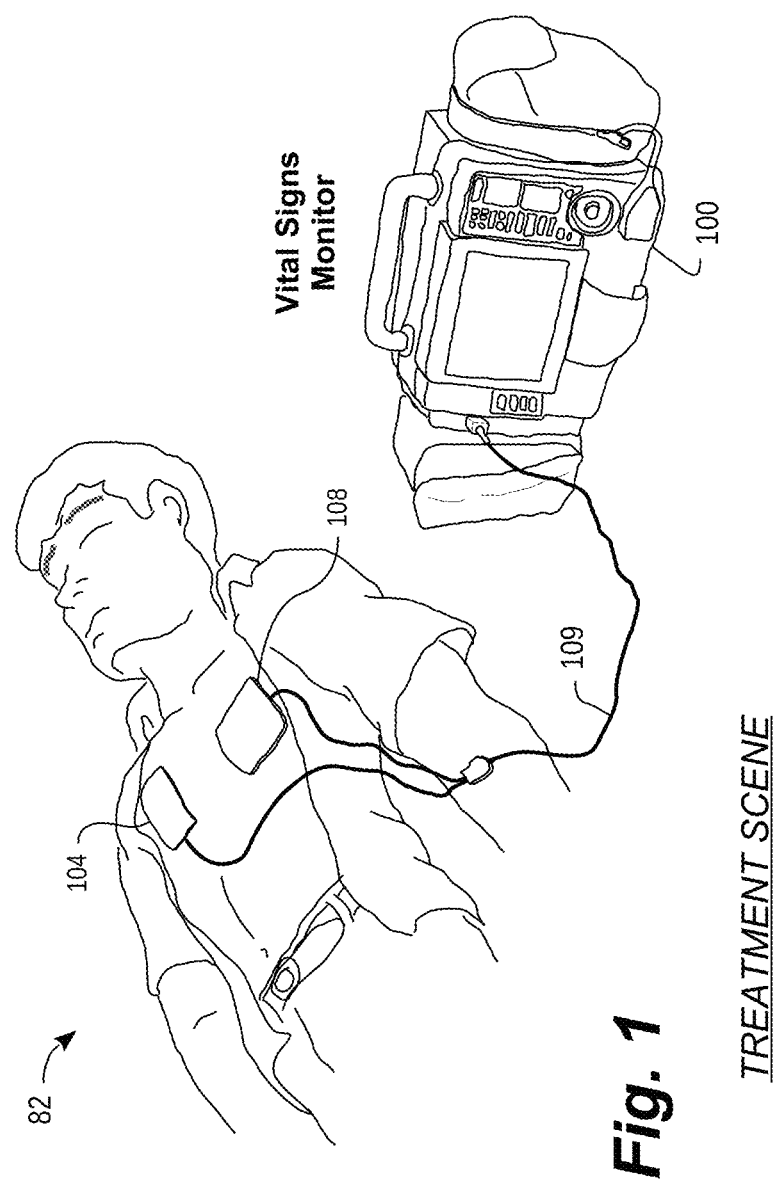
FIG. 1 is a diagram of a medical treatment scene where a patient is being treated for an acute medical condition that benefits from monitoring at least some of the patient's vital signs, such as heart rate and blood pressure.

Generally stated, embodiments of this disclosure measure two values which can be used to compute a patient's instantaneous blood pressure. Embodiments of this disclosure measure the instantaneous Non-Invasive Blood Pressure (NIBP) of a patient with an apparatus that determines the values for, in one example, two of the unknowns in the water hammer equation: pulse wave velocity (PWV) and instantaneous blood velocity (Vi). The water hammer equation relates instantaneous blood pressure to pulse wave velocity and blood flow velocity as follows:

$$P_i = \rho PWV v_i$$

where PWV is the pulse wave velocity, $\rho$ is the density of the blood which may be assumed to be a constant, for example, vi is the instantaneous velocity of the blood, and Pi is the desired instantaneous blood pressure.

Some conventional NIBP measurement systems rely on PWV to measure NIBP, but each requires an initial calibration measurement, taken at least once, to convert a relative blood pressure value to an actual blood pressure value. The required calibration measurement is taken using a traditional blood pressure cuff, for example on the arm or perhaps the finger. Such conventional NIBP measurement systems that require an initial calibration and all calculations are based on a difference or differential value of that initial calibration measurement to achieve an actual measurement.

The disclosed NIBP systems and devices instead take an instantaneous blood pressure measurement rather than a change from an initial calibration measurement. Avoiding the need for a calibration measurement, prevents the patient from experiencing blood flow restriction altogether. Although PWV is highly correlated with blood pressure (BP) so that changes in blood pressure can be calculated from changes in PWV by relying on an initial calibration measurement relatively accurately, what has not been solved until now is how to eliminate the need to acquire and use a separate, initial calibration value or values to register a particular PWV to a particular value of blood pressure (as opposed to simply a change in blood pressure) for a patient. State of the art of NIBP using PWV typically uses a standard cuff-based measurement, to interrupt the blood flow, to measure and associate a particular blood pressure to a particular PWV measurement in a patient. Interrupting the blood flow requires that the patient's appendage being measured is compressed to restrict the blood flow. Such restriction of the patient's blood flow prevents such conventional methods of measuring blood pressure from being applied to areas of the patient's body that cannot withstand restricted blood flow, such as a patient's neck, for example.

In this way, conventional methods and devices that provide NIBP measurements using PWV require a distinct calibration step. In contrast to the state of the art, the disclosed embodiments include a method and device that eliminate the requirement of a distinct calibration step, especially using a technology that temporarily restricts blood flow. In short, the disclosed embodiments include self-calibrating NIBP systems and methods using PWV, or alternatively, NIBP systems and methods using PWV without the temporary interruption of blood flow.

The lack of need for a calibration step for devices using the method taught herein arises from the use of the water hammer equation in its integrated (non-differential) form. In the water hammer equation, the blood pressure is related to the PWV by a scale factor that can be known without a distinct calibration step. The scale factor is found using the same ultrasound technology that is used to measure the PWV. That scale factor is related to the blood velocity and blood density. In this way, a particular blood pressure is calculated as the PWV scaled by the blood density and the blood velocity.

Blood velocity can be acquired using ultrasound as a time varying waveform. PWV can also be measured with ultrasound also as a time varying function. The time-varying nature of the PWV means that it can be updated from beat to beat if desired. The time-varying nature of the blood velocity means that blood velocity can be measured at a much finer resolution than a cardiac cycle, that is to say, continuously during the cardiac cycle for as many cardiac cycles as is desired. Because blood density is already sufficiently known and is relatively constant, not only can a particular blood pressure measurement be known as if it were obtained by a standard cuff-based measurement, but all manners of blood pressure measurements can be made as time-varying waveforms describing the instantaneous pressure at as many points during a cardiac cycle as desired. That is to say, blood pressure can be monitored continuously throughout the cardiac cycle with as fine a resolution as is required, and this can be done for as many contiguous cardiac cycles as is desired for beat-to-beat monitoring, or as intermittently as desired.

Measuring the instantaneous blood pressure instead of its change relative to a calibrated baseline measurement means, for example, that as arterial walls stiffen (due to disease, drug therapy, and/or normal vasculature responses, for example) which increases the PWV, this new PWV value is measured along with any corresponding change in blood velocity to produce an updated blood pressure waveform. Additionally, if the heart pumps more or less energetically, the blood velocity changes accordingly, which results in the blood pressure changing proportionately, all else equal. This updated blood velocity measurement at the prevailing PWV (which characterizes the state of the vasculature) corresponds to the updated blood pressure after being scaled by blood density. In other words, since there are two measurements made, PWV and blood velocity, and not just PWV alone, a distinct calibration step is not needed, as the ambiguity of PWV by itself is remedied by adding the second measured value of blood velocity. This is of great value over conventional patient NIBP monitoring using PWV alone where typically the calibration step requires a blood pressure measurement performed by restricting blood flow, which can be more costly, time consuming, and/or uncomfortable to the patient. In the embodiments discussed below, ultrasound technology is used to acquire both the PWV and the blood velocity although other methods of obtaining the PWV and the blood velocity can alternatively or additionally be used. Further embodiments implement various techniques and devices to measure or detect both pulse wave velocity and instantaneous blood velocity. As is described in greater detail below, specific embodiments simplify the task of measuring NIBP without sacrificing reliability. Still further, embodiments enable the measurement of (or at least an estimation of) NIBP without requiring calibration that relies on a separate means for detecting blood pressure, which simplifies the treatment and evaluation of the patient.

This disclosure begins with a description of one example of a medical device that may be used in specific embodiments. Next is a discussion of one embodiment of a sensor for measuring NIBP using ultrasound. Alternative embodiments for sensors which measure NIBP are further discussed.

Description of Operative Environment for Embodiments

FIG. 1 is a diagram of a medical treatment scene. As illustrated, a person 82 is lying supine. Person 82 could be a patient in a hospital or someone found unconscious. Person 82 is experiencing a medical condition which requires monitoring of the person 82. Person 82 may be a victim of cardiac arrest, or some other emergency, and consequently a patient.

In the example shown in FIG. 1, a portable vital signs monitor 100 has been brought close to person 82. The vital signs monitor can also be, for example, a hybrid monitor/defibrillator. As illustrated, a number of physiologic sensors may be attached to person 82, such as vital signs monitoring (VSM) sensors 104, 108, and connected to vital signs monitor 100. The vital signs monitor 100 provides a user with information about the vital signs of person 82 collected using VSM sensors 104, 108. Vital signs monitor 100 can be one of many different types, such as a monitor or monitor/defibrillator, each with different sets of features and capabilities. The set of capabilities of vital signs monitor 100 is determined, generally, by who would use it, and what training they would likely have. Although illustrated as a vital signs monitor in FIG. 1, many other medical devices may be used in the medical treat ent scene, and may implement various embodiments of the disclosure.

Figure 2:
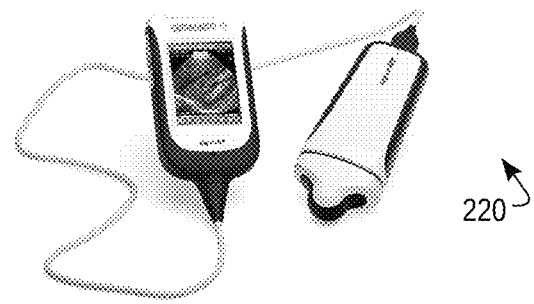
FIG. 2 is a conceptual illustration of a number of medical devices in which embodiments of the disclosure may be implemented.
Figure 2:
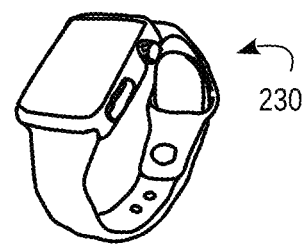
Figure 2:
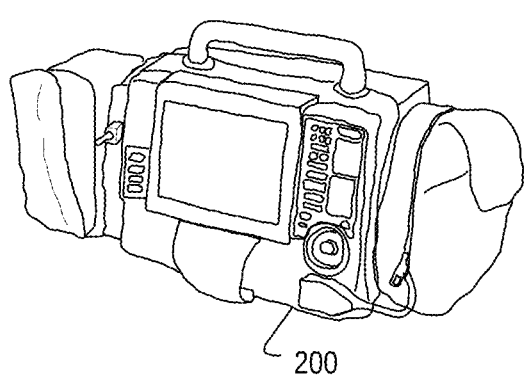
Figure 2:
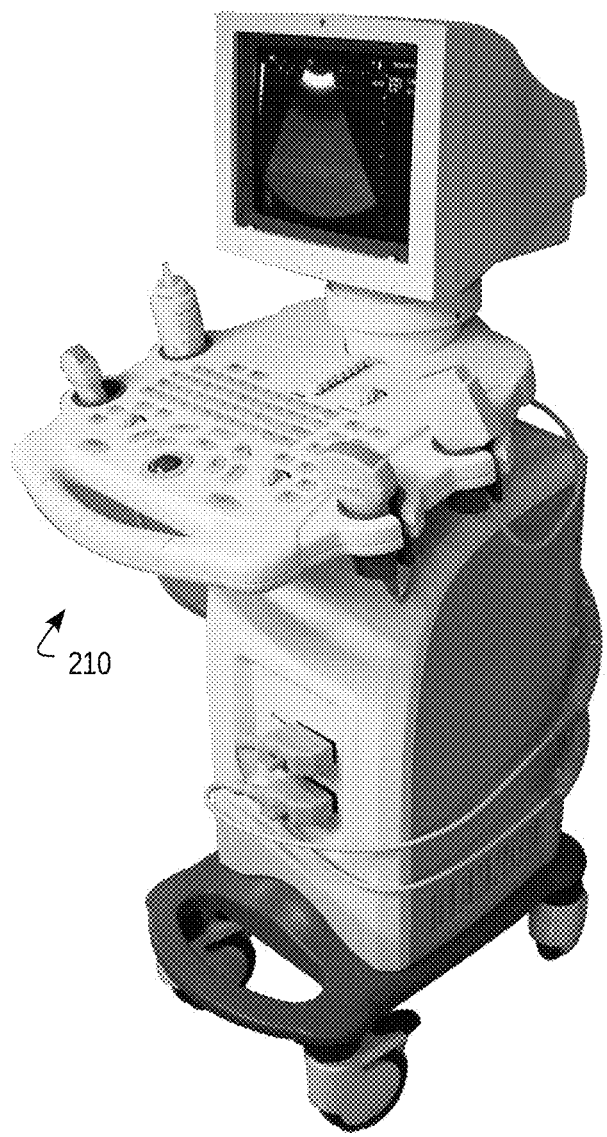

Turning briefly to FIG. 2, various medical devices in which embodiments may be implemented are shown. By way of example, embodiments may be implemented in a monitor/defibrillator 200. A defibrillator-monitor (or monitor-defibrillator) is typically formed as a single unit with a defibrillator in combination with a patient monitor. Alternatively, the defibrillator-monitor may be a modular device with separable components. For example, in one embodiment, the defibrillator-monitor may include a base component and a plurality of detachable pods. Each pod may communicate with the base component, perhaps wirelessly. Certain pods may be used to collect information about a patient, such as vital statistics.

As a patient monitor, the device 200 may have features additional to what may be needed, but can be there should a need arise or because they are customized to a person. These features can be for monitoring physiological indicators of a person in an emergency scenario. These physiological indicators are typically monitored as signals, such as a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

In addition, embodiments may be implemented in an ultrasound machine 210. As shown in FIG. 2, an ultrasound machine 210 may be variously sized and shaped, although common ultrasound machines are adapted to be deployed at bedside, such as may be used in a hospital or other controlled health care environment.

In the illustrated embodiment, the ultrasound machine 210 may include a chassis and a transducer. The chassis, for example, may be made of molded plastic, metal, or some combination of both. The chassis houses a module for generating electrical signals which are conveyed to the transducer to be transformed into ultrasonic energy. The transducer transmits ultrasound waves into a subject (e.g., a patient) by converting the electrical signals to ultrasonic energy. The transducer further receives ultrasound waves backscattered from the subject by converting received ultrasonic energy to analog electrical signals.

The ultrasound machine 210 may also include an operator interface through which an operator inputs information to affect the operating mode of the ultrasound machine. Through the interface, the ultrasound machine 210 may also output status information for viewing by the operator. The interface may provide a visual readout, printer output, or an electronic copy of selected information regarding the examination.

Other embodiments may be implemented as a standalone device, such as a handheld. NIBP monitor 220. The handheld NIBP monitor 220 may be sized and configured for easy portable use. In such a case, the handheld NIBP monitor 220 may include a transducer and a housing. The transducer of the handheld NIBP monitor 220 may operate in similar fashion to the transducer of the ultrasound machine 210. Likewise, electronic components that perform computational functions may be contained within the housing.

Yet other embodiments may be implemented as an ultraportable device (e.g, wearable NIBP monitor 230), such as a smartwatch, wearable bracelet, wearable adhesive sensor, or the like. In such an embodiment, components of the transducer may be integrated into a unitary housing and attached or affixed to a person for vital signs monitoring.

Illustrative examples of various devices, including medical devices, show various embodiments. However, the scope of this disclosure is not limited to these embodiments and the disclosure may be implemented in many other embodiments not shown or described. For example, embodiments may be implemented within electronic wearable devices, such as a smartwatch or other wireless-enabled portable electronic device, or other smart wearables, such as sensor clothing or skin prints. In one specific example, an electronic piece of jewelry (or the like) may be implemented which includes ultrasound sensing technology that is capable of measuring or estimating non-invasive blood pressure based on the teachings of this disclosure. All such embodiments are within the teachings of this disclosure and fall within the scope of the appended claims.

Figure 3:
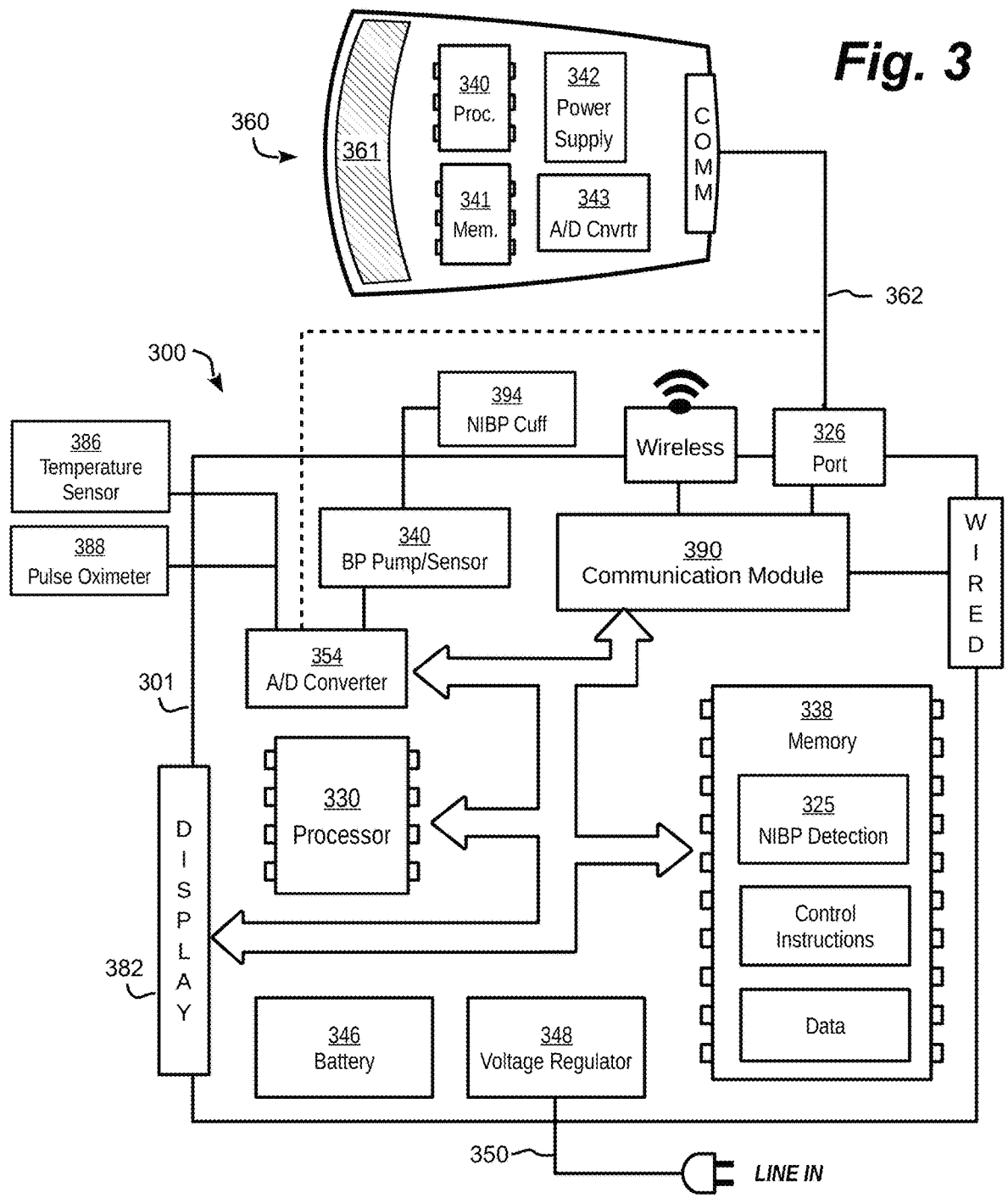
FIG. 3 is a diagram showing components of a medical device in which embodiments of the disclosure may be implemented.

FIG. 3 is a diagram showing components of a medical device made according to embodiments. In this particular example, the medical device is a vital signs monitor 300, although many components are common to other medical devices. These components can be, for example, in vital signs monitor 100 of FIG. 1. The components shown in FIG. 3 can be provided in a housing 301, also known as a casing.

It will be appreciated that, in other embodiments, these components may be implemented in separate housings or as sub-components of various other devices.

In this illustrative embodiment, vital signs monitor 300 includes a processor 330 and a memory 338. The processor 330 is a computing component operative to execute programming instructions. The processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs); Programmable Logic Devices (PLDs); Application Specific Integrated Circuits (ASICs), any combination of one or more of these; and so on.

The memory 338 stores instructions (e.g., programs or applications) to be executed by processor 330 and can also store data collected from various physiological sensors used with the vital signs monitor. For example, memory 338 can store patient data, such as, for example, blood pressure measurements taken or computed by the vital signs monitor 300. In addition, memory 338 can store prompts for the user, etc. Memory 338 may be implemented in any number of ways. Such ways include, by way of example and not of limitation; nonvolatile memories (NVM), read-only memories (ROM), random access memories (RAM), any combination of these, and so on.

Processor 330 is further preferably connected to a display screen 382, which can also be remote from the sensor. If display screen 382 is a touch sensitive screen, microprocessor 330 can both send data to and receive data from the display screen 382. The processor 330 can further optionally communicate with other external computing peripherals (not shown), such as a personal computer and/or an external printer.

Various sensors are included for detecting physiologic characteristics of a patient. For instance, a temperature sensor 386 and a pulse oximeter sensor 388 may be connected to processor 330 via A/D converter 354. A/D converter 354 is capable of converting analog data to digital data, and digital data to analog data. A NIBP cuff (or sphygmomanometer cuff) 394 is pneumatically connected to a blood pressure pump 340 used to pressurize the blood pressure cuff 394. Like the pulse oximeter sensor 388 and temperature sensor 386, blood pressure sensor 340 is connected to A/D converter 354. Those skilled in the art will understand that use of fully digital sensors can eliminate analog to digital conversion of sensor signals and thus eliminate A/D converter 354.

The vital signs monitor 300 preferably receives power by a line voltage connection 350 regulated by at least one voltage regulator 348. However, the vital signs monitor 300 may also rely on a battery 346 as a power source. Reliance on battery power may be advantageous in some circumstances because it allows the vital signs monitor 300 to be portable. It should be understood that voltage regulator 348 may be configured to produce a number of different power outputs connected to a number of different components. The sensor may also wirelessly collect ambient energy from available sources (not shown) especially when neither battery nor line voltage are available.

Vital signs monitor 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, cardiopulmonary resuscitation (CPR) performance, blood pressure, and so on.

In one embodiment, vital signs monitor 300 further includes an ultrasound transducer 360. The transducer 360 is preferably enclosed in a case to insulate it from electrical interference. The transducer 360 includes, in this embodiment, an active element 361 is made of piezoelectric material (e.g., PZT) or, alternatively, micromachined ultrasonic transducers (MUT) or other MEMS devices (e.g., PMUT devices, or the like). The active element 361 may be a single element or an array. The active element 361 is responsible for radiating an ultrasound wave and detecting reflected signals, in this embodiment. The active element 361 may, in some embodiments, employ separate transmitting and receiving elements. Alternatively, other embodiments may combine both functions into a single piezoelectric transceiver, or other sensor technology or material that converts mechanical energy to electrical energy and vice versa.

In one embodiment, a connection 362 couples the transducer 360 to the vital signs monitor 300 for operative communication. Connection 362 is illustrated in FIG. 3 as an ordinary wire or similar direct electrical connection (either detachable or fixed) between the transducer 360 and the vital signs monitor 300. Alternatively, the connection 362 may be a wireless connection between the transducer 360 and a wireless transceiver of the vital signs monitor 300 (e.g., communication module 390).

In some embodiments, transducer 360 may deliver an analog signal or signals to the vital signs monitor 300. In such an embodiment, connection 362 may route through A/D converter 354 (illustrated in dashed line) where the analog signals are converted to digital signals which may be operated upon by processor 330. In other alternatives, the transducer 360 may deliver either a combination of analog and digital signals, or all digital signals. In such a case, the connection 362 may either partially or entirely avoid the A/D converter 354.

In some embodiments, the transducer 360 is a peripheral component of the vital signs monitor 300. In such embodiments, transducer 360 may rely on the computational functions of the vital signs monitor 300. In other embodiments, the transducer 360 may be a completely self-contained item. In such embodiments, the transducer 360 may further include its own computational components, such as a dedicated processor 340, memory 341, A/D converter 343, and power supply 342.

In one embodiment, the vital signs monitor 300 includes an NIBP detection component 325. In one specific implementation, the NIBP detection component 325 includes functions which, when executed by processor 330, operate to measure a patient's blood pressure based on at least a sound wave analysis. The NIBP detection component 325 may be coupled to the transducer 360 via a port 326, which causes a sound wave to be generated and transmitted, via the transducer 360, to a patient. A return signal received at the transducer may be communicated back to the NIBP detection component 325 via the transducer port 326 using connection 362.

In alternative embodiments where the transducer 360 is self-contained, the NIBP detection component 325 could be implemented in the memory 341 of the transducer 360 for execution by the processor 340. In yet another alternative, the NIBP detection component 325 may be remotely executable, via connection 362, using the processor 340 of the transducer 360.

In accordance with various embodiments, the NIBP detection component is configured to perform a sound wave analysis that determines, for example, two values: a pulse wave velocity and an instantaneous blood velocity. The NIBP detection component 325 is further configured to compute an instantaneous blood pressure based on the pulse wave velocity and the instantaneous blood velocity. The pulse wave velocity computation may be performed by analyzing ultrasound imaging, such as B-mode, M-mode, or 2D-mode imaging, combined with physical dimensions either directly measured or computed using data received through the sound wave analysis. The blood velocity computation may be implemented as any appropriate Doppler detection technique, for example, such as by correlation (e.g., autocorrelation, cross-correlation, or the like) or Fourier transform processing, to determine Doppler characteristics of blood within a vessel.

NIBP detection component 325 may provide notice of its analysis in many ways. In one example, the NIBP detection component 325 may be an automatic detector which provides an on-screen indication, via display 382, of its analysis. Alternatively, NIBP detection component 325 may output to a more direct indicator, such as a speaker or other output.

Embodiments of the disclosure implement various techniques and devices to measure or detect both pulse wave velocity and instantaneous blood velocity. As is described in greater detail below; specific embodiments simplify the task of measuring NIBP without sacrificing reliability.

Various other components may also be used to provide added functionality not shown. Non-exhaustive examples of such components include a speaker, microphone, digital camera interface, additional environmental or physiological sensors, accelerometers, and the like.

Illustrative Embodiments of the Disclosure

Figure 4:
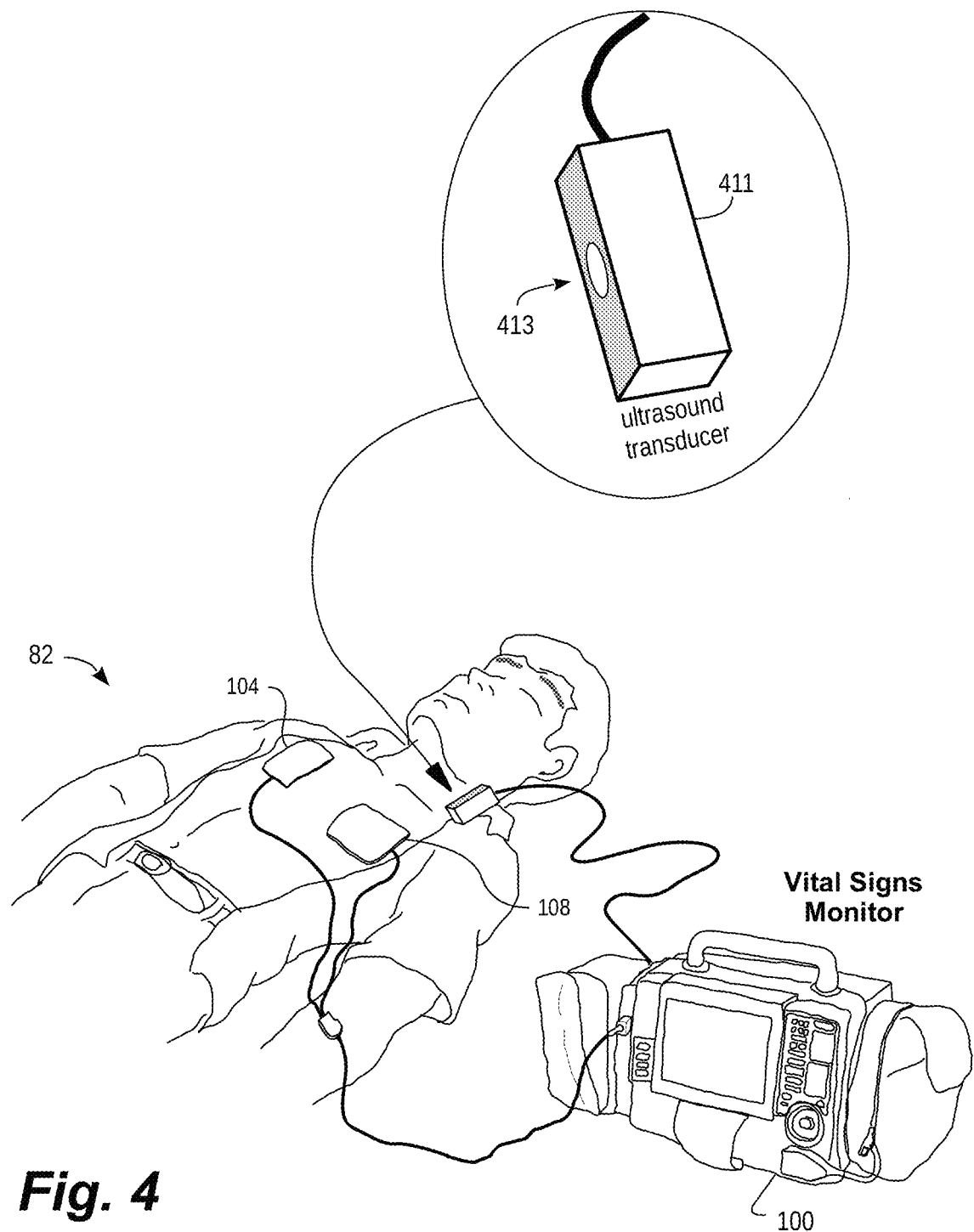
FIG. 4 is a conceptual diagram of one embodiment of the disclosure.

FIG. 4 is a conceptual diagram of one embodiment of the disclosure. As shown in FIG. 4, one embodiment for measuring NIBP employs an ultrasound transducer 411 that may be affixed to a patient (e.g., patient 82) adjacent to any appropriate vein or artery. As illustrated, the ultrasound transducer 411 is affixed to the patient 82 adjacent to the patient's carotid artery.

In this particular embodiment, the ultrasound transducer 411 is implemented with a single sensor 413, which reduces size and cost, Alternative implementations and embodiments may employ more sensors in addition to the single ultrasound sensor. In use, ultrasound transducer 411 may self-dispense a wetting agent, such as ultrasound gel, to eliminate air from between the patient's skin and ultrasound sensor 413. To enhance reliability, the field of view and the signal to noise ratio should be significantly high enough to allow the sensor to be easily applied and still achieve good results.

As noted above, embodiments of the disclosure measure the patient's pulse wave velocity and instantaneous blood velocity, which then reveal the patient's NIBP via the water hammer equation, There are a number of different techniques for measuring each of PWV and blood velocity. However, implementations of the embodiment measure both as discussed here. Certain alternative implementations and embodiments are discussed later in this document.

Figure 5:
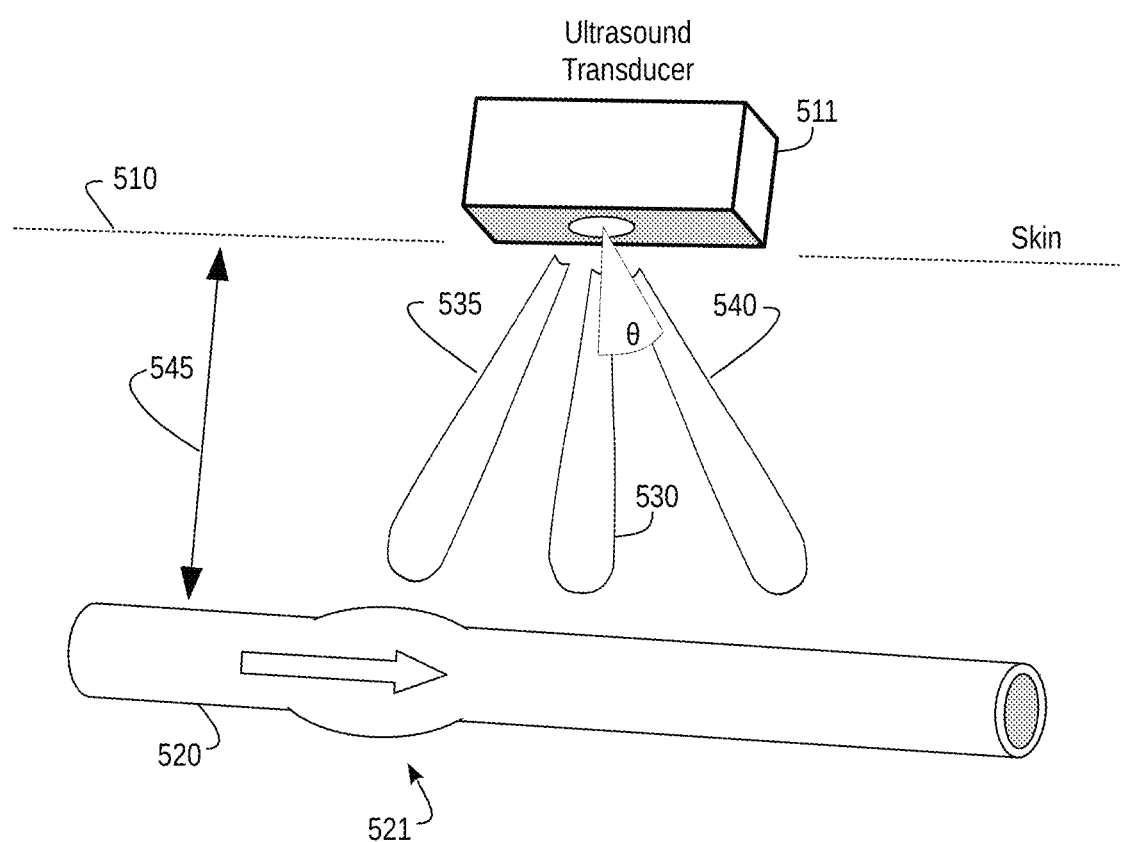
FIG. 5 is another a conceptual illustration of one implementation of an embodiment in operation.

Turning now to FIG. 5, a conceptual illustration is shown of one implementation of an embodiment in operation. As shown in FIG. 5, an ultrasound transducer 511 is affixed to a patient's skin 510 with the axis of the ultrasound transducer 511 roughly aligned parallel to a proximate vessel, such as a vessel located in the neck or arm or finger, where the direction is known, A proximate vessel is a blood vessel in the patient that is being used to measure the patient's blood pressure and can be both a targeted blood vessel chosen to be used as the vessel within which the blood pressure is measured or can be a blood vessel that is found through discovery by or a vessel that is simply nearby the disclosed NIBP devices and/or systems. In this particular example, a carotid artery 520 is selected because of its relative ease of access and relatively linear presentation. The construction of the sensor in the perpendicular axis is either sufficiently narrow so that the field of view is wide or is augmented with a lens that achieves a wide field of view from a larger element. In this way, the sensor is able to be placed with a correct orientation so that a proximate vessel is within the field of view of the sensor. In one embodiment, the transducer 511 may be curved to provide a larger field of view.

In one embodiment, ultrasound waveforms of the length of about 1 mm and of a center frequency of about 6 MHz are pulsed at a repetition rate of up to 10 kHz. The ultrasound waveforms are composed of a main lobe 530 and two grating lobes (left grating lobe 535 and right grating lobe 540). Other components of the ultrasound waveforms which may be present are not illustrated. In one embodiment, the ultrasound transducer 511 is constructed such that the active pressure sensitive areas of its single sensor are interdigitated with inactive areas having a periodic spacing so that the grating lobes (535, 540) are intentionally formed at a desired separation angle $\theta$. By so doing, accurate distance measurements may be obtained between any two points in the field of view of the sensor using triangulation techniques.

Generally stated, this implementation of the embodiment radiates ultrasound waveforms as discussed above. The return signals are used in two ways: to determine pulse wave velocity and to determine instantaneous blood velocity. With those two values, the patient's NIBP may be determined using, for example, the water hammer equation. Generally stated, this embodiment detects pulse wave velocity by analyzing blood wave motion using, for example, B-mode or M-mode images captured by the ultrasound transducer. In addition, blood velocity is determined by analyzing the Doppler effect on the return signals.

Measuring Pulse Wave Velocity

Blood pumping through the vessel 520 causes a localized expansion (pulse 521) in the vessel 520. Knowing the rate at which the pulse 521 travels along a given distance in a given time provides the pulse wave velocity. To make that determination, the ultrasound transducer 511 identifies the vessel wall motion as the pulse 521 moves past the left grating lobe 535, main lobe 530, and right grating lobe 540.

The most identifiable return signal will be the specular reflection from the main lobe 530, A depth 545 of the vessel 520 directly under the sensor 511 is derived from the location of the specular response. The depth 545 of the vessel 520 and the grating lobe angle $\theta$ reveal the slant range depth of the vessel 520 at the point of incidence of both the left grating lobe 535 and the right grating lobe 540.

Blood vessel wall motion may then be identified by cross correlation between small regions at the same time vicinity corresponding to the slant range depth of the vessel, that is, around the point in tinge the signal returns from the intersection of the ultrasound beam and vessel. The pulse wave velocity is calculated as the distance along the vessel 520 between any two lobes (e.g., the two grating lobes, either grating lobe and the main lobe, or the like) divided by the time between motion at the slant range depths corresponding to the pulse 521 passing by those two lobes.

The time may be measured to as low as 100 microsecond resolution and can be interpolated for finer resolution. Pulse wave velocities are typically in the 6 to 10 m/sec range. For grating lobes to be 2 cm apart at the vessel depth, the time for the pulse wave to pass from, for example, one grating lobe to another would be as short as 2 milliseconds which is 20 times larger than the 100 microsecond resolution of the disclosed embodiment. It should be appreciated that ultrasound shear wave imaging techniques may also be used to measure pulse wave velocity.

Measuring Instantaneous Blood Velocity

Using the same data, the velocity of the blood may also be measured using ultrasound pulse wave Doppler (PWD) techniques. This is accomplished by performing Doppler analysis in the vicinity of the vessel center. This Doppler analysis identifies the phase change of the returned signal from the blood between each of the 10 kHz repetitions after filtering out any static returns. The phase change of the returned signal over a corresponding change in time is the blood velocity.

In one embodiment two measurements are made as blood flow towards the transducer 511 can be resolved from blood flow away from the transducer 511. This velocity is then corrected by the sine of the known grating lobe angle $\theta$ normal to the transducer 511, For small vessels (where the 1 mm pulse length encompasses much of the diameter of the vessel), this integrated velocity may be mapped to a true instantaneous velocity at the center of the vessel based upon previously gathered empirical databases or tabulated or computed relationships between mean blood flow and peak blood flow under various flow conditions and vessel sizes.

Once the instantaneous blood velocity and the pulse wave velocity are known, instantaneous blood pressure is computed using the water hammer equation. Again, the blood density may be treated as a constant to yield the NIBP, Alternatively, the actual blood density of the patient may be used in the equation if that value is known, such as from prior testing or analysis.

Figure 6:
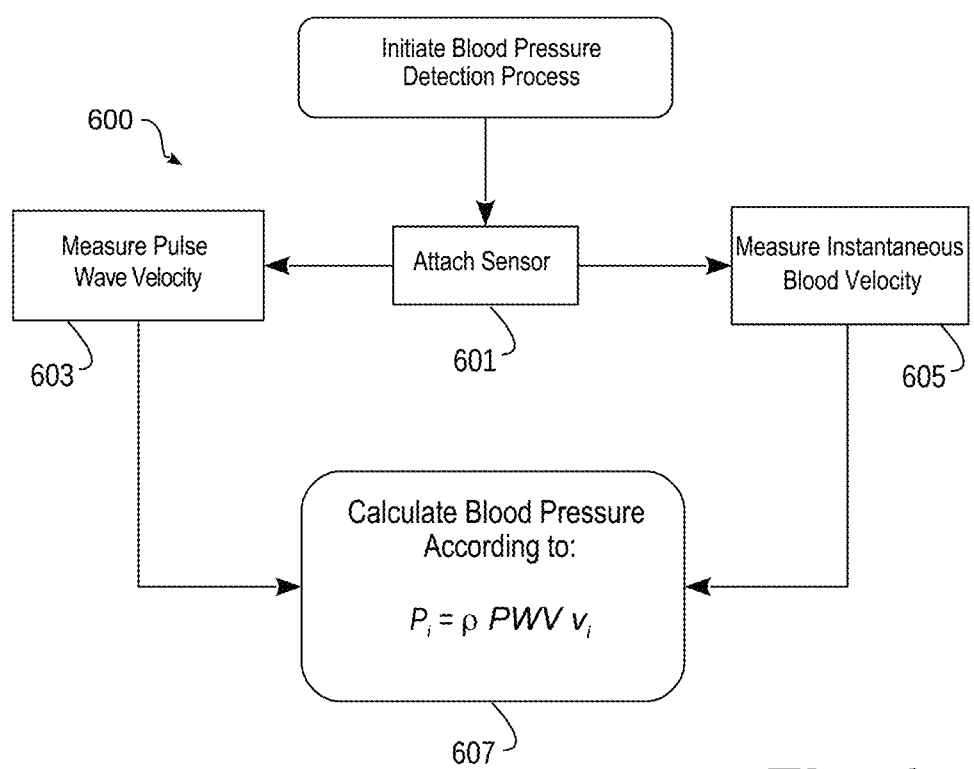
FIG. 6 is a conceptual flow diagram of a method that implements one embodiment for measuring non-invasive blood pressure.

Turning briefly to FIG. 6, a conceptual flow diagram is shown that implements one method 600 for measuring non-invasive blood pressure. To begin, the method 600 starts when a sensor configured in accordance with embodiments of this disclosure is attached to a patient (step 601). As discussed at length above, the sensor includes an ultrasound sensor and may include one or more alternative sensors.

In its most basic form, the method 600 proceeds by substantially simultaneously measuring pulse wave velocity (step 603) and instantaneous blood velocity (step 605). Although summarized here, each of those two basic steps may be accomplished in numerous ways.

For example, pulse wave velocity may be measured using a sound analysis based on information known about the configuration of the sensor. In one specific embodiment, the sensor is configured such that an ultrasound waveform radiated by the sensor will produce grating lobes having known characteristics, such as a grating lobe separation angle of $\theta$. The sound analysis may further compute a depth from the sensor to a subject blood vessel. Based on those data, ultrasound imaging combined with triangulation techniques may be used to compute a rate at which a pulse travels through the vessel, thereby revealing the pulse wave velocity of the vessel.

Similarly, instantaneous blood velocity may be measured using Doppler effect techniques. In one specific embodiment, the Doppler analysis may identify the phase change of a returned signal from the blood between each of the 10 kHz repetitions.

Once pulse wave velocity and instantaneous blood velocity are known, the method 600 continues by calculating the instantaneous blood pressure (step 607) in accordance with, for example, the water hammer equation. Based on that equation, pulse wave velocity, instantaneous blood velocity, and blood pressure are related as follows:

$$P_i = \rho PWV v_i$$

Once calculated, the blood pressure measurement may be presented to a user for use in treatment of the patient. It should be appreciated that, in another alternative, continuous wave Doppler (CWD) may be used as an alternative to pulse wave Doppler (PWD).

Alternative Embodiments of the Disclosure

Although the embodiment discussed above is one embodiment, many other embodiments may also be implemented which employ the teachings of this disclosure. Discussed here are but a few of the many alternative embodiments which implement this disclosure.

Figure 7:
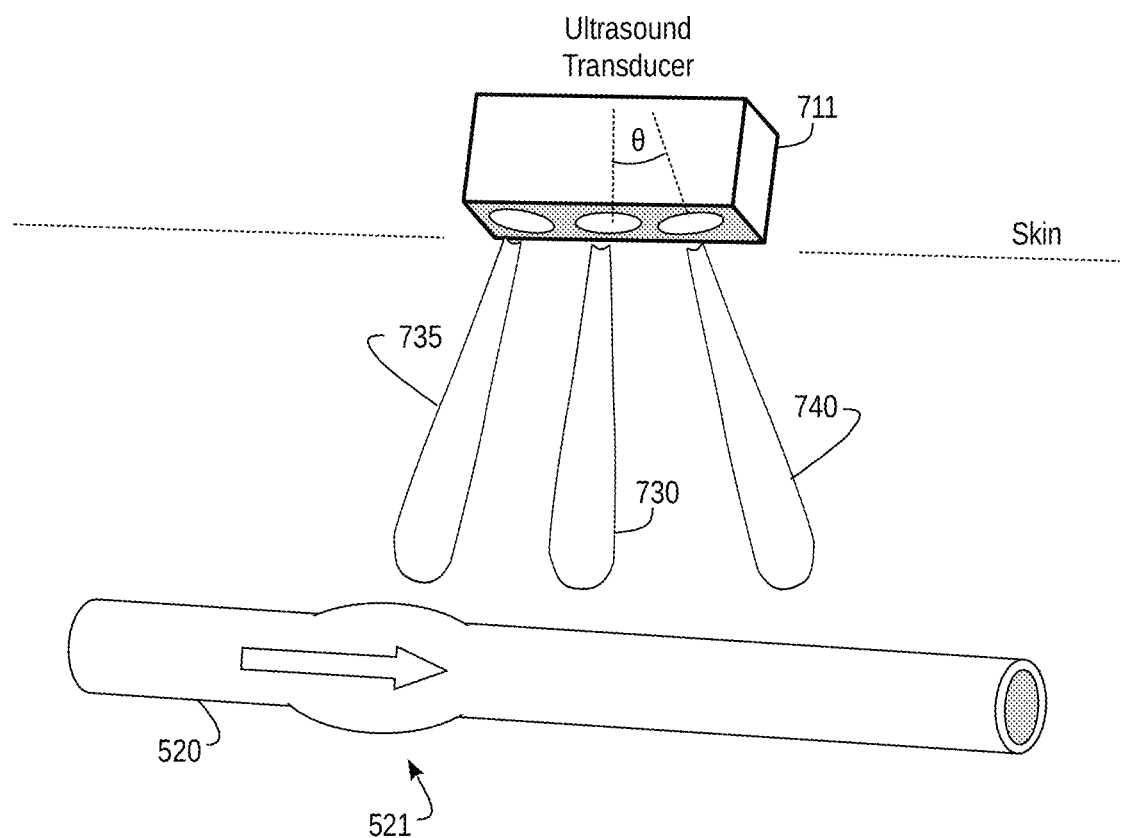
FIG. 7 is a conceptual illustration of one alternative embodiment that uses two or more elements rather than a single sensor.

FIG. 7 is a conceptual illustration of one alternative embodiment which uses two or more elements rather than a single sensor. For example, a composite sensor of two or three elements r ray be implemented such that each element does not have a grating lobe but are mounted at known angles such as the grating lobe angle in the figure below. Each sensor would need its own analog path to digitization. Such a sensor could be integrated with other sensors such as pulse oximetry.

Figure 8:
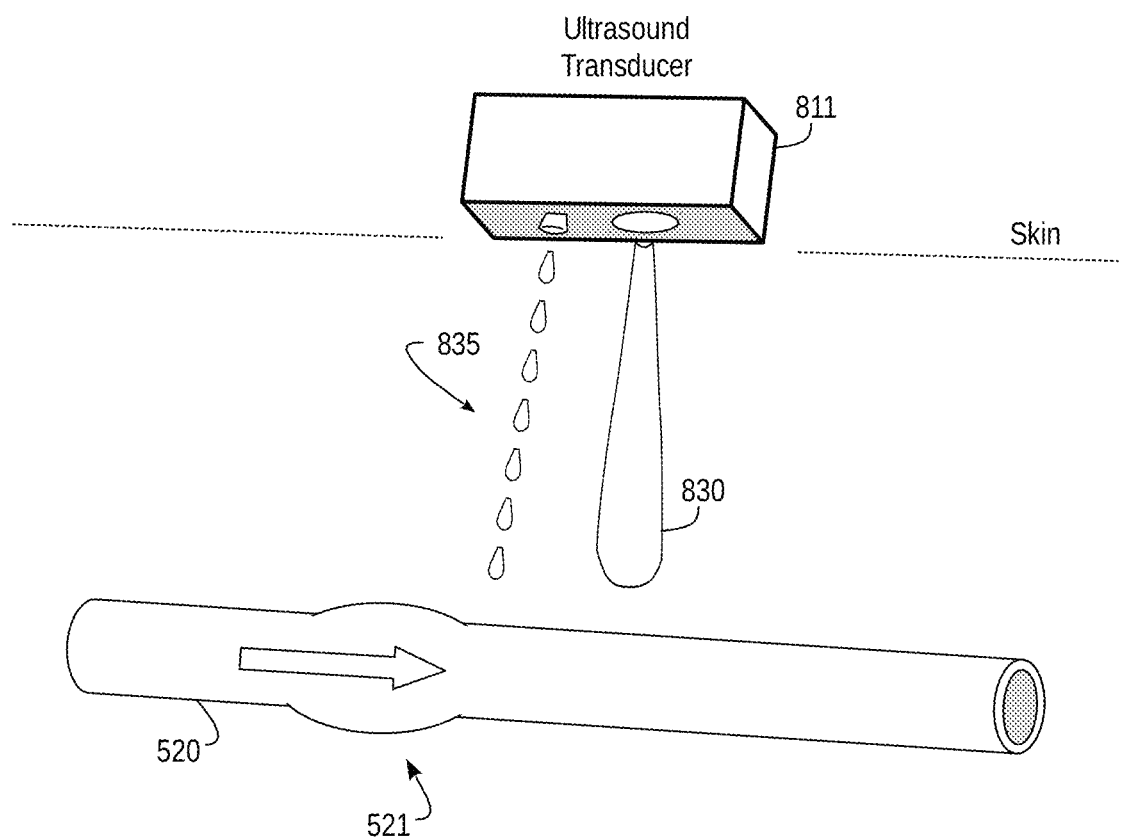
FIG. 8 is a conceptual illustration of another alternative embodiment which implements an ultrasound sensor in combination with a sensor based on a different technology.

FIG. 8 is a conceptual illustration of another alternative embodiment which implements an ultrasound sensor in combination with a sensor based on a different technology. Other techniques are emerging for measuring pulse wave velocity which may be combined, in certain embodiments, with an ultrasound sensor to detect instantaneous blood pressure. Accordingly, the alternative embodiment illustrated in FIG. 8 implements an optical sensor which is employed to determine velocity of pulse 521 within vessel 520. The alternative embodiment shown in FIG. 8 makes use of an ultrasound sensor radiating an ultrasound waveform 830 in combination with a second sensor radiating a second signal 835 based on some other technology, such as a light emitting diode or the like.

In this particular embodiment, the transducer assembly 811 is illustrated as a standalone component. However, in other embodiments the transducer assembly 811 may be combined with or integrated into another component. In one example, a portable external monitor-defibrillator may be specially configured to support the Doppler detection of NIBP. In such an embodiment, the transducer assembly 811 may be combined with or integrated into a set of ECG leads, one or more defibrillation electrodes, or some other component of a vital signs monitor. In this way, the function of detecting NIBP may be incorporated into a medical device which is already in use in medical emergency situations, thereby eliminating a need to employ yet another, separate medical device.

Many other embodiments are also envisioned to be within the scope of the disclosure. For example, embodiment that are implemented in devices other than medical devices (e.g., exercise equipment, or other non-medical equipment) are also envisioned. Similarly, embodiments that compute or estimate blood pressure by virtue of a non-invasive measurement of two or more characteristics of a patient using an equation other than the water hammer equation are also possible. Any appropriate equation which associates blood pressure to measurable characteristics of a patient's physiology other than the blood pressure are also envisioned.

In summary, the disclosed embodiments overcome shortcomings of existing systems by obviating the need to manually attempt to detect non-invasive blood pressure by using a cuff, or the like. In these and other ways, which will become apparent upon a study of the disclosed teachings, these embodiments provide a superior treatment technique and transducer assembly for the non-invasive detection of blood pressure in a patient.

Other embodiments may include combinations and sub-combinations of features described above or shown in the Figures, including, for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, "feature" or "features" can refer to structures and/or functions of an apparatus, article of manufacture or system, and/or the steps, acts, or modalities of a method.

It should be readily apparent to those skilled in the art that what is described herein may be modified in numerous ways. Such ways can include equivalents to what is described herein. In addition, the invention may be practiced in combination with other systems. The following claims define certain combinations and sub-combinations of elements, features, steps, and/or functions, which are regarded as novel and non-obvious. Additional claims for other combinations and sub-combinations may be presented in this or a related document.

What is claimed is:

1. A device, comprising:
    an ultrasound transducer assembly configured to:
        emit an ultrasound signal toward a blood vessel, the ultrasound signal comprising a first grating lobe and a second grating lobe, a center of the first grating lobe and a center of the second grating lobe being nonparallel;
        receive a reflection of the first grating lobe from a first portion of a wall of the blood vessel;
        receive a reflection of the second grating lobe from a second portion of the wall of the blood vessel;
    a processor; and
    memory storing instructions that, when executed by the processor, cause the processor to perform operations comprising:
        identifying, based on the reflection of the first grating lobe from the first portion of the wall of the blood vessel, a movement of the first portion of the wall of the blood vessel;
        identifying, based on the reflection of the second grating lobe from the second portion of the wall of the blood vessel, a movement of the second portion of the wall of the blood vessel;
        determining a pulse wave velocity of the blood vessel based on an angle between the first grating lobe and the second grating lobe, the movement of the first portion of the wall of the blood vessel, and the movement of the second portion of the wall of the blood vessel;

determining, based on the reflection of the second grating lobe from blood flowing through the blood vessel, an instantaneous blood velocity of the blood flowing through the blood vessel; and determining, based on the pulse wave velocity and the instantaneous blood velocity, a blood pressure of the blood vessel.

2. The device recited in claim 1, wherein determining, based on the pulse wave velocity and the instantaneous blood velocity, the blood pressure of the blood vessel is based on a product of the pulse wave velocity, a density of the blood, and the instantaneous blood velocity.

3. The device recited in claim 1, wherein the device comprises a monitor.

4. The device recited in claim 1, wherein the device comprises an ultrasound machine.

5. The device recited in claim 1, wherein the device comprises a wearable device that is configured to be affixed to a patient.

6. The device recited in claim 1, wherein determining, based on the pulse wave velocity and the instantaneous blood velocity, a blood pressure of the blood vessel is performed without reference to a separate blood pressure measurement performed using another device.

7. The device recited in claim 1, wherein the ultrasound transducer assembly, the memory, and the processor are contained within a disposable housing.

8. The device recited in claim 1, wherein the device is further configured to transmit an indication of the blood pressure to a separate device.

9. The device recited in claim 1, wherein the device is configured to dispense a gel.

10. The device recited in claim 1, wherein the operations further comprise:
identifying a diameter of the blood vessel.

11. The device recited in claim 1, wherein the operations further comprise:
identifying, based on the reflection of the second grating lobe from the blood flowing through the blood vessel, a net flow of the blood through the blood vessel.

12. The device recited in claim 1, wherein determining the pulse wave velocity is based on a time interval between the movement of the first portion of the wall of the blood vessel and the movement of the second portion of the wall of the blood vessel.

13. The device recited in claim 1, wherein determining the pulse wave velocity is based on a distance between the ultrasound transducer assembly and the wall of the blood vessel.

14. The device of claim 1, wherein determining-the pulse wave velocity is based on a time of the movement of the first portion of the wall of the blood vessel and a time of the movement of the second portion of the wall of the blood vessel.

15. The device of claim 1, wherein determining the instantaneous blood velocity comprises:
determining a phase difference between the second grating lobe and the reflection of the second grating lobe from the blood flowing through the blood vessel; and
determining the instantaneous blood velocity based on the phase difference, wherein the reflection of the second grating lobe from the blood flow through the blood vessel is from a center of the blood vessel.

16. The device of claim 1, wherein the blood vessel is located in a neck of an individual.

17. The device of claim 1, wherein the first grating lobe and the second grating lobe comprise 10 kHz ultrasound pulses with a center frequency of 6 MHz.

18. The device of claim 1, wherein the device is a smartwatch.

19. The device of claim 1, wherein the device is a defibrillator and further comprises: a defibrillation electrode integrated with the ultrasound transducer assembly.

20. The device recited in claim 1, wherein the ultrasound transducer assembly comprises a single sensor configured to emit the first grating lobe and the second grating lobe.

21. The device recited in claim 1, wherein the first grating lobe and the second grating lobe are separated by an inactive space.

22. A device, comprising:
an ultrasound transducer configured to:
transmit an ultrasound signal toward a blood vessel, the ultrasound signal comprising a first grating lobe transmitted toward a first portion of a wall of the blood vessel and a second grating lobe transmitted toward a second portion of the wall of the blood vessel, a center of the first grating lobe and a center of the second grating lobe being nonparallel;
receive a reflection of the first grating lobe from the first portion of the wall of the blood vessel; and
receive a reflection of the second grating lobe from the second portion of the wall of the blood vessel; and
a processor configured to:
identify, based on the reflection of the first grating lobe from the first portion of the wall of the blood vessel, a movement of the first portion of the wall of the blood vessel;
identify, based on the reflection of the second grating lobe from the second portion of the wall of the blood vessel, a movement of the second portion of the wall of the blood vessel;
determine an instantaneous blood flow value corresponding to a velocity of blood flowing through the blood vessel;
identify a velocity of a pulse wave moving along the blood vessel based on the movement of the first portion of the wall of the blood vessel, the movement of the second portion of the wall of the blood vessel, and an angle between the first grating lobe and the second grating lobe; and
determine a blood pressure based on the velocity of the blood flowing through the blood vessel and the velocity of the pulse wave moving along the blood vessel.

23. The device recited in claim 22, wherein the processor determines the blood pressure based on a product of the velocity of the pulse wave moving along the blood vessel, a density of blood, and the velocity of the blood flowing through the blood vessel.

24. The device recited in claim 22, further comprising a cuff that is configured to be attached to a person, the cuff comprising the ultrasound transducer.

25. The device recited in claim 24, wherein the processor is configured to determine the blood pressure without reference to a blood pressure measurement performed using another device.

26. The device recited in claim 22, wherein the ultrasound transducer and the processor are contained within a disposable housing.

27. The device recited in claim 22, wherein the device is further configured to transmit the blood pressure to a separate device.

28. The device recited in claim 22, wherein the device is configured to dispense a gel.

29. The device recited in claim 22, wherein the device is powered by a battery.

30. The device recited in claim 22, wherein the processor is further configured to:
identify a diameter of the blood vessel.

31. The device recited in claim 22, wherein the processor is further configured to:
identify, based on the velocity of the blood flowing through the blood vessel, a net flow of the blood.

32. The device recited in claim 22, wherein the ultrasound transducer comprises a single sensor configured to emit the first grating lobe and the grating second lobe.

33. A method for non-invasively measuring a blood pressure, comprising:
transmitting an ultrasound signal toward a blood vessel, the ultrasound signal comprising a first grating lobe transmitted toward a first portion of a wall of the blood vessel and a second grating lobe transmitted toward a second portion of the wall of the blood vessel, a center of the first grating lobe being nonparallel with a center of the second grating lobe;
receiving a reflection of the first grating lobe from the first portion of the wall of the blood vessel;
identifying a movement of the first portion of the wall of the blood vessel based on the reflection of the first grating lobe from the first portion of the wall of the blood vessel;
receiving a reflection of the second grating lobe from the second portion of the wall of the blood vessel;
identifying a movement of the second portion of the wall of the blood vessel based on the reflection of the second grating lobe from the second portion of the wall of the blood vessel;
identifying a blood velocity of blood flowing through the blood vessel;
identifying a pulse wave velocity based on the movement of the first portion of the wall of the blood vessel, the movement of the second portion of the wall of the blood vessel, and an angle between the first grating lobe and the second grating lobe; and
computing the blood pressure as a function of the blood velocity and the pulse wave velocity.

34. The method recited in claim 33, wherein computing the blood pressure is based on a product of the pulse wave velocity, density of the blood, and the blood velocity.

35. The method recited in claim 33, wherein the blood pressure is computed without reference to a separate blood pressure measurement.

36. The method recited in claim 33, wherein identifying the pulse wave velocity is based on a distance between the ultrasound transducer and the blood vessel.

37. The method recited in claim 33, wherein the first grating lobe and the second grating lobe are transmitted by a single sensor.

* * * * *